United States Patent [19]
Meade

[11] Patent Number: 6,030,623
[45] Date of Patent: Feb. 29, 2000

[54] MEDICAL EXTRACT FROM PLANT

[76] Inventor: William H. Meade, 2019 Valley View Dr., Claremore, Okla. 74017

[21] Appl. No.: 09/183,121

[22] Filed: Oct. 30, 1998

[51] Int. Cl.$^7$ .................................................. A01N 65/00
[52] U.S. Cl. ........................................................ 424/195.1
[58] Field of Search .......................................... 424/195.1

[56] References Cited

U.S. PATENT DOCUMENTS

| | | | |
|---|---|---|---|
| 4,511,555 | 4/1985 | Faust | 424/74 |
| 5,529,778 | 6/1996 | Rohatgi | 424/195.1 |
| 5,627,216 | 5/1997 | Papadopoulos | 514/783 |
| 5,698,206 | 12/1997 | Becker et al. | 424/401 |

OTHER PUBLICATIONS

Scisearch Computer Abstract Peterson et al Physiological Entomology Sep. 1993. vol. 19, No. 3 pp. 285–295.

*Primary Examiner*—Herbert J. Lilling
*Attorney, Agent, or Firm*—Molly D. McKay

[57] ABSTRACT

The present invention is a process of extracting canna plant leaves and the resulting two medicinal chemical compositions thus produced by the process. The process produces a first chemical composition consisting of a water-and-oil extract of dried canna plant leaves and a second chemical composition consisting of the extracted residue from this extraction process. The extract and the extracted residue may be taken orally by a patient, and the extract may also be applied topically. The process consists of extracting dried and pulverized canna plant leaves with a water-and-oil mixture by simmering the leaves in the mixture for about a day. The extract is decanted, filtered and ready for use. The remaining residue is dried, further ground, and encapsulated in gelatin capsules for ease in oral administration.

4 Claims, No Drawings

MEDICAL EXTRACT FROM PLANT

BACKGROUND OF THE INVENTION

1. Field of the Invention

The present invention relates to a water-and-oil extract of canna plants and a residue from the extraction process that each has medicinal uses. Dried canna leaves are simmered for several hours in water and Egyptian oil, i.e. a mixture of olive oil, peanut oil, sassafras oil and pine needle oil. The extract may be taken orally or may be applied topically to treat a wide range of ailments. The extracted leaves are dried and ground and then placed in gelatin capsules to be taken orally to also treat a wide range of ailments.

2. Description of the Related Art

Plants and plant extracts have been used for years to treat a wide range of ailments in men and animals. These plants and plant extracts have been either applied topically to the affected area of the body or have been taken internally by the patient.

The present invention is the result of the Inventor's quest to find a treatment that would cure a skin condition that had plagued the Inventor for many years and for which the medical profession could provide no permanent cure. After many years of research and testing, the present invention has been created as a treatment for a wide variety of skin conditions, including psoriasis, skin cancer, fingernail and toenail fungus, discolored moles, and scarring. Initial clinical testing of the invention indicates that the extract and the extracted residue produced are efficacious in the treatment of certain carcinomas and some skin conditions. The invention was also found to have a definite angiogenesis inhibitory effect on both benign and malignant tumors. Additional side effects that were observed in clinical test patients included extra energy, increased fingernail thickness and strength, and stimulation of the immune system. It is postulated that the invention may also be useful in treating spider veins and varicose veins, chronic diarrhea, chronic sinus problems, all types of cancer, blood disorders, high blood sugar, osteoporosis, hepatitis, sore throats, influenza, and HIV/AIDS.

SUMMARY OF THE INVENTION

The present invention is a process and the resulting chemical compositions thus produced by the process. The process produces a chemical composition consisting of a water-and-oil extract of dried canna plant leaves and a chemical composition consisting of the extracted residue from this extraction process. Both the extract and the extracted residue are produced for medicinal purposes. Both the extract and the extracted residue may be taken orally by a patient and the extract may also be applied topically.

The process consists of harvesting canna plant leaves, drying them, and then grinding or pulverizing them to the consistency of cigarette tobacco. Next, the dried and pulverized leaves are placed in a heated container containing a mixture of water and Egyptian oil and simmered at a temperature just below the boiling point of the mixture for about twenty four (24) hours. Egyptian oil is available commercially and contains a mixture of olive oil, peanut oil, sassafras oil and pine needle oil. Although Egyptian oil has been shown to be effective, other types and mixtures of oils may prove to be just as effective in practicing the invention. After the mixture has simmered a sufficient length of time, the liquid is decanted, filtered and bottled for topical or oral use. The residue remaining in the container is removed, dried, further ground or pulverized, and placed in gelatin capsules that may be taken orally by a patient.

DETAILED DESCRIPTION OF THE PREFERRED EMBODIMENT INVENTION

The present invention is a process and the resulting chemical compositions thus produced by the process. The process produces a medicinal chemical composition consisting of a water-and-oil extract of dried canna plant leaves and a medicinal chemical composition consisting of the extracted residue from this extraction process. Both the extract and the extracted residue may be taken orally by a patient, and the extract may also be applied topically.

The process by which the two medicinal chemical compositions are produced consists of first of harvesting and drying leaves of the canna plant. Canna plants, which are also known as Indian shot, belong to a genius of tropical plants also known as canna indica. They are common garden plants that are grown from tubers and some varieties grow up to approximately seven feet in height. Canna plants normally flower all summer and bear multiple flowers on the top of the stalks. Canna flowers may be red, orange, yellow or variegated. At the present it appears that any variety of canna leaves will suffice in practicing the present invention, although further research may indicate one or more types to be preferred.

The leaves are preferably hung to air dry in a process that is similar to drying of tobacco leaves. Once the leaves are dried, they are then reduced to the consistency of cigarette tobacco by grinding or pulverizing them. It is thought that by thus increasing the surface area of the dried leaves, the efficiency of the extraction step is facilitated.

Next, the dried and pulverized leaves are placed in a heated container. Distilled water and oil are also added to the heated container in the approximate proportions of 96 ounces of distilled water and 64 ounces of oil to each gallon of dried and finely ground canna leaves. The oil that is used in this extraction process is preferably Egyptian oil. Although Egyptian oil has been shown to be effective, other types and mixtures of oils may prove to be just as effective in practicing the invention. Egyptian oil may be obtained commercially from Heritage Products, Box 444, Virginia Beach, Va. 23458, and consists of a mixture of olive oil, peanut oil, sassafras oil and pine needle oil.

The leaves, water, and oil mixture is then heated to a temperature just below the boiling point of the mixture and is simmered at this temperature for about twenty four (24) hours. The extraction time is not critical, but sufficient simmering time is needed in order for the canna leaves to be extracted. One indicator that the leaves have simmered sufficiently is that the mixture will become dark in color and opaque. After the mixture has simmered a sufficient length of time, the liquid is decanted from the remaining solid residue. The liquid is then filtered to clarify it and to remove any remaining entrained particles. At this point the liquid is ready for use and may be bottled for later topical or oral use.

The remaining solid residue that is left in the container after the liquid portion is removed is then also removed from the container and is dried. The residue may be dried either by air drying or by use of a dehydrator. The dried mixture is the further ground or pulverized to a fine powder and is then placed in gelatin capsules that may be taken orally by a patient.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A chemical composition for topical and oral medicinal use comprising:

a water-and-oil extract of dried canna leaves wherein the oil in the water-and-oil extract consists of a combination of peanut oil, olive oil, conifer needle oil, and sassafras oil.

2. A chemical composition according to claim 1 wherein the water-and-oil extract comprises a mixture of distilled water and oil that has been simmered with dried canna leaves, decanted therefrom and filtered.

3. A chemical composition for oral medicinal use comprising:

dried canna leaves that have been extracted with water and a mixture of peanut, olive, conifer needle, and sassafras oils by simmering the water and oil mixture with the canna leaves and that have been re-dried and pulverized after being extracted with the water and oil mixture.

4. A chemical composition for oral medicinal use according to claim 3 wherein said re-dried and pulverized canna leaves are encapsulated in gelatin capsules.

* * * * *